(12) United States Patent
Lucht et al.

(10) Patent No.: US 10,266,695 B2
(45) Date of Patent: Apr. 23, 2019

(54) **CULTIVATION OF *XYLARIA* SPECIES BIOMASS AS A BINDING AGENT IN MATERIAL PRODUCTION**

(71) Applicants: Matthew Lucht, Troy, NY (US); Jacob Winiski, Troy, NY (US); Sue Van Hook, Cambridge, NY (US); Alex Carlton, Troy, NY (US); Gavin McIntyre, Troy, NY (US)

(72) Inventors: Matthew Lucht, Troy, NY (US); Jacob Winiski, Troy, NY (US); Sue Van Hook, Cambridge, NY (US); Alex Carlton, Troy, NY (US); Gavin McIntyre, Troy, NY (US)

(73) Assignee: Ecovative Design LLC, Green Island, NY (US)

( * ) Notice: Subject to any disclaimer, the term of this patent is extended or adjusted under 35 U.S.C. 154(b) by 261 days.

(21) Appl. No.: 15/096,856

(22) Filed: Apr. 12, 2016

(65) Prior Publication Data

US 2016/0302364 A1 Oct. 20, 2016

Related U.S. Application Data

(60) Provisional application No. 62/147,338, filed on Apr. 14, 2015.

(51) Int. Cl.
| | |
|---|---|
| *C08L 97/02* | (2006.01) |
| *A01G 18/00* | (2018.01) |
| *C12N 1/14* | (2006.01) |
| *C12N 1/22* | (2006.01) |

(52) U.S. Cl.
CPC .............. *C08L 97/02* (2013.01); *A01G 18/00* (2018.02); *C12N 1/14* (2013.01); *C12N 1/22* (2013.01)

(58) Field of Classification Search
None
See application file for complete search history.

(56) References Cited

FOREIGN PATENT DOCUMENTS

CN 101653081 A * 2/2010

OTHER PUBLICATIONS

Visser ("Pseudoxylaria as stowaway of the fungus-growing termite nest: Interaction asymmetry between Pseudoxylaria, Termitomyces and free-living relatives" Fungal Ecology, 2011, 322-332) (Year: 2011).*
Ugalde ("Chapter 11: Autoregulatory Signals in Mycelial Fungi", The Mycota: A Comprehensive Treatise on Fungi as Experimental Systems for Basic and Applied Research, Second Edition, Edited by K. Esser, Springer, Berlin Germany 2006, 203-213), (Year: 2006).*

* cited by examiner

*Primary Examiner* — Louise W Humphrey
*Assistant Examiner* — Charles Zoltan Constantine
(74) *Attorney, Agent, or Firm* — Francis C. Hand; Carella, Byrne, Bain, Gilgillan, Cecchi, Stewart & Olstein

(57) ABSTRACT

The process aseptically inoculates a liquid media with a vegetative *Xylaria* fungal species to form a culture; statically incubates the culture in a vessel for a time sufficient to begin initiation of fruit body development and asexual sporulation and halts incubation at maximum conidia production prior to the beginning of sexual sporulation. Thereafter, the entire culture contents of the incubation vessel are macerated to homogenize the fungal biomass and conidia therein and form an inoculum.

18 Claims, 6 Drawing Sheets

CULTIVATION OF *XYLARIA* SPECIES BIOMASS AS A BINDING AGENT IN MATERIAL PRODUCTION

This application claims the benefit of U.S. Provisional Patent Application No. 62/147,338, filed Apr. 14, 2015.

This invention relates to a process for generating fungal biomass through cultivation of species from the genus *Xylaria*. More particularly, this invention relates to a process for generating fungal biomass through cultivation of *Xylaria polymorpha*.

BACKGROUND

*Xylaria* species are generally saprophytic, soft rot ascomycetes that primarily grow on decaying hardwoods. During vegetative growth this fungus extends white, monomitic mycelium to capture nutritional resources. After external stimuli initiate fruiting, the outer mycelium surface differentiates and forms black-pigmented stromatic tissue. Ascocarps (fruiting bodies) then elongate and extend upwards as they mature.

Fully mature fruiting bodies in the wild can be 3-10 cm tall and up to 2.5 cm wide. These fungi have an extended fruiting cycle (3-4 months) consisting of an initial phase where diploid asexual conidia are produced on the outer fruit body surface and a later phase where perithecia eject haploid sexual ascospores. When in this younger stage, the asexual conidia-producing conidiophores are closely packed on the stroma surface.

Published US Patent Application 2014/0186,927 describes a process for the production of a chlamydospore rich slurry inoculum for use in inoculating a solid or liquid substrate, such as described in published US Patent Application 2008/0145,577. As is known in the prior art, a concentrated mass of asexual spores can be used as an effective inoculum. Chlamydospores generated within normal vegetative growth can be distributed and function as discrete points of inoculation. This is dependent upon the natural ability of the fungus to sporulate extensively in the mycelium. Such behavior is completely independent of hyphal differentiation towards fruiting body development.

Spore mass inoculation has also been suggested in Published US Patent Application 2005/0176583. The described method of spore production is reliant upon development of fully mature fruiting bodies on a solid substrate and submersing the fruiting bodies in water to capture the released sexual spores. The total process time from solid substrate inoculation to mature sporocarp harvest can take anywhere from 30-60 days. The inoculum produced through this process is completely composed of sexual spores without incorporating mycelium or fruit body tissue.

OBJECTS OF THE INVENTION

Accordingly, it is an object of the invention to reduce the time for generating a biomass for use as an inoculum.

It is another object of the invention to reduce the time for generating a biomass for use as a binding resin.

It is another object of the invention to streamline the process for generating a biomass for use as an inoculum or binding resin.

BRIEF SUMMARY OF THE INVENTION

Briefly, the invention provides a process for generating a biomass comprising the steps of (1) preparing a liquid medium including a carbon source, a nitrogen source and micronutrients; (2) inoculating the liquid media aseptically with a vegetative *Xylaria* fungal species to form a culture; (3) statically incubating the culture in a vessel for a time sufficient to begin initiation of fruit body development and asexual sporulation; (4) halting incubation at maximum conidia production prior to the beginning of sexual sporulation; and (5) thereafter macerating the entire culture contents of the incubation vessel to homogenize the fungal biomass and conidia therein and form an inoculum.

The behavior of *Xylaria* species allows for the development of a novel process that carries the benefits of asexual spore mass inoculation, while remaining reliant upon the growth of fruiting bodies and not upon sporulation within the mycelium.

It is understood that the process is particularly effective with a vegetative *Xylaria* fungal species selected from the group consisting of *Xylaria polymorpha*, *Xylaria hypoxylon*, *Xylaria filiformis* and *Xylaria longipes*.

In accordance with the invention, a mass of tissue is generated on liquid media, which can then be induced to differentiate and produce numerous fruiting bodies within the same culture vessel. However, the ascocarps do not need to reach full sexual maturity due to the primary asexual sporulation phase. This reduces the total growth time from inoculation to ascocarp harvest from 60 days to 14-21 days.

The entire fungal mass can then be blended and diluted to function as inoculum.

The process of the invention incorporates the asexual conidia, vegetative hyphae, and fruit body tissue within the same inoculum providing additional points of inoculation compared to the prior art. As a means of generating large masses of fungal biomass with high biological efficiency, this process greatly improves yield with a 41% increase in biomass compared to typical vegetative sheet biomass production.

The process of the invention can be used to make a fungal inoculum or a fungal biomass for use as a binding resin.

In order to make a binding resin, the inoculum is combined with particles, such as lignocellulosic particles, incubated for a time sufficient for hyphae to form a network around the particles and to bond the particles into a cohesive biomass and thereafter the resulting cohesive biomass is set as a resin. In particular, the *Xylaria* species form dense networks around the individual particles (instead of binding particles together) as well as penetrate and form cavities within the particle cells.

In making a fungal inoculum, the process is simplified by eliminating the need for isolation of spores from fruiting bodies or depending upon sporulation within the mycelium. All components of the tissue culture are included in the inoculum (asexual conidia and mycelium), which reduces processing time while potentially increasing the concentration of discrete points of inoculation.

In making a binding resin, the process generates a fungal biomass per surface area of growth media that is 30% to 50% greater than typical vegetative tissue cultures due to the prolific production of fruiting bodies with a homogenous stroma layer over the vegetative tissue layer. The binding resin can then be used with discrete particles or in the casting of complex shapes.

These and other objects and advantages of the invention will become more apparent from the following detailed description taken in conjunction with the accompanying drawings wherein.

Figure 4A:
Figure 4B:
Figure 4C:
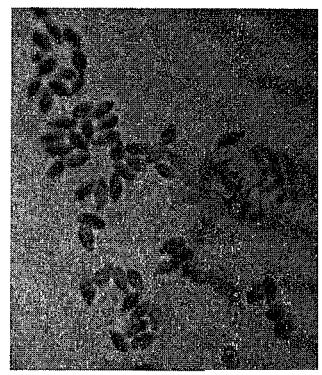
Figure 5A:
Figure 5B:
Figure 5C:
Figure 6:
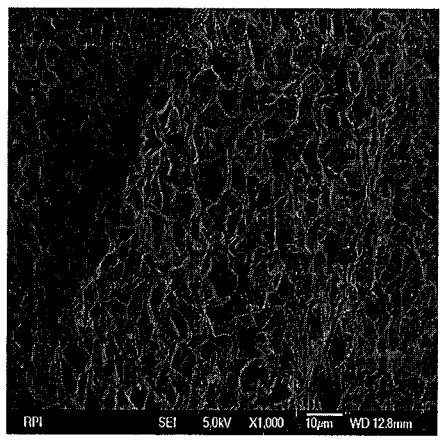

FIGS. 4a and 4b pictorially illustrate views of developing ascocarps after 15 days of incubation;

FIG. 4c pictorially illustrates a view of isolated conidia after 15 days of incubation;

FIGS. 5a, 5b and 5c pictorially illustrate views of elongated ascocarps after 45 days of incubation; and FIG. 6 pictorially illustrates a view of a scanning electron micrograph (SEM) of a biomass made in accordance with invention after compression.

DETAILED DESCRIPTION

Figure 1:
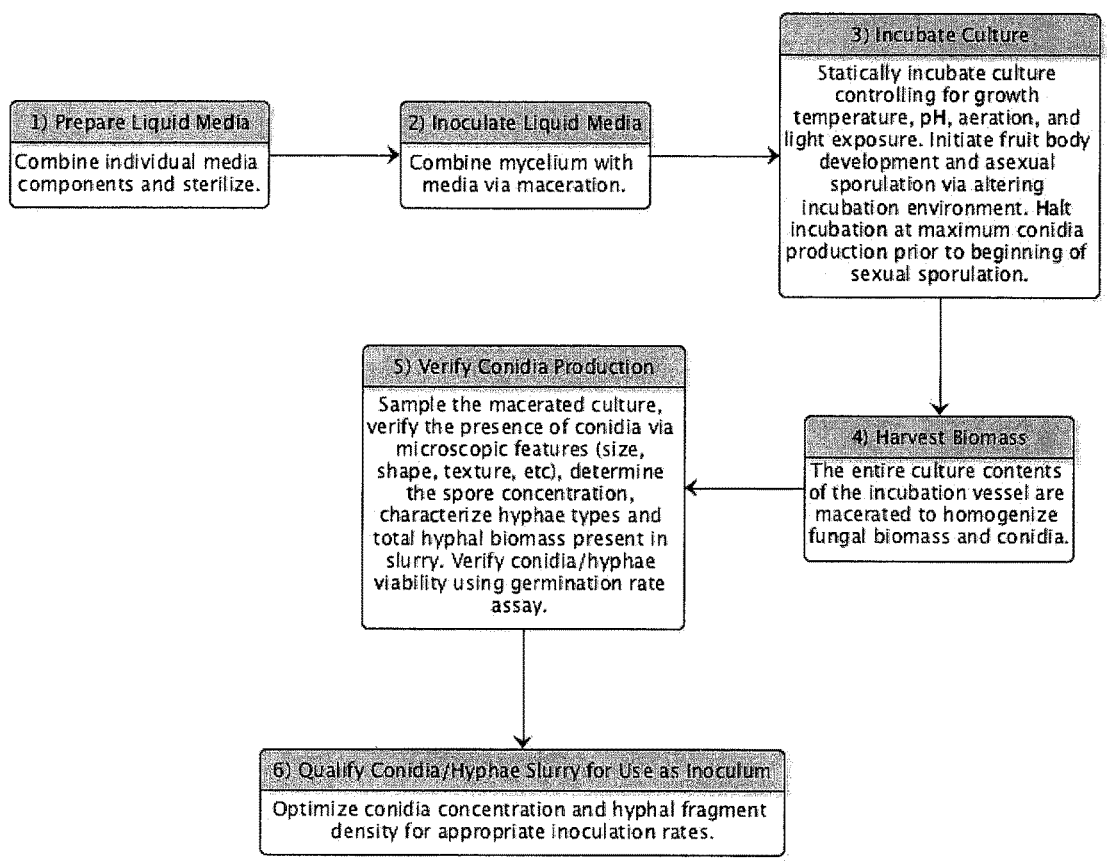
FIG. 1 illustrates a flow diagram of a process for making an inoculum in accordance with the invention.

Referring to FIG. 1, the process for producing an inoculum requires the following steps:

Step 1—Preparation of a Liquid Media.

A liquid growth medium is prepared by mixing:
a. Carbon Source: simple sugars, starch, malt extract
b. Nitrogen Source: Peptone, yeast extract, soy protein
c. Water The amounts of the components are as follows:
Carbon Source: 8-15 g
Nitrogen Source: 0.5-4 g
Water: 1 L After mixing of the media components, the mixture of components is sterilized at 15 psi and 121° C. for 15 minutes.

Step 2—Inoculation of Liquid Media

The sterile liquid growth medium of step 1 is then inoculated aseptically by combining with a previously prepared vegetative fungal tissue (I.e. mycelium) at a rate of 0.01-5% of mycelium to the sterile liquid growth medium (v/v=volume of inoculum added per unit volume of media) via maceration to obtain a culture.

Step 3—Incubation of Culture

The inoculated culture of step 2 is incubated in a static culture vessel under strict environmental conditions, i.e.
  a. Growth temperature maintained between 20° C. and 30° C.
  b. pH of media buffered to maintain 5-7 during growth
  c. No exposure to light/UV
  d. Oxygen/carbon dioxide exchange within the culture vessel maintained to promote vegetative exponential growth
    a. 12-22% Oxygen
    b. 1-8% Carbon dioxide
  e. Time: until vegetative growth develops a homogeneous mycelium layer across the entire liquid surface, usually, between 5 and 7 days
  f. Induction of ascocarp (fruiting body) development
    a. Cycling of temperatures from 15° C. to 30° C. in 12 hour periods to mimic day/night cycles. High temperatures maintained during the "day" cycle and temperature is gradually reduced for the "night" cycle.
    b. Cycling of oxygen/carbon dioxide concentrations by increasing gas exchange to maintain typical atmospheric oxygen and carbon dioxide levels
    c. Cycling of light/UV exposure from no light exposure to 6 to 18 hours of light exposure followed by a period of no light exposure.

During this step, the inoculated culture is statically incubated (i.e. not stirred or agitated). Fruiting body development and asexual sporulation are initiated by altering the incubation environment once a homogeneous mycelium layer develops across the entire liquid surface.

Incubation is halted at maximum conidia production prior to the beginning of sexual sporulation. Maximum conidia production is indicated when ascocarps drop a visible layer of conidia en masse from the fruiting bodies, usually between days 14 and 21.

Step 4—Harvesting of Biomass

After incubation of step 3, the entire culture contents of the incubation vessel are macerated to homogenize fungal biomass and conidia. Any remaining undigested sugars or extracellular growth factors are maintained in the spent culture fluid and are carried through as a part of the inoculum.

Step 5—Verification of Conidia Production

The homogenized biomass from step 4 is analyzed for adequate asexual sporulation and vegetative hyphae development by taking a sample of the biomass.
  a. Verification of the presence of conidia is made via microscopic features, i.e. conidia are observed via light microscopy to verify diagnostic features, such as, size, shape, texture, presence/absence of germ slit, color. A germ slit is an opening in the spore cell wall where the germinating mycelium emerges. This characteristic is only present in the sexual ascospores and not the asexual conidia.
  b. Concentration of conidia (spore concentration) is confirmed via hemocytometer spore counts of culture liquid
  c. Characterization of the hyphae types is made e.g. vegetative hyphae are observed via light microscopy to determine physical characteristics, such as, hyphae types, range of fragment lengths, hyphal fragment density (concentration)
  d. Determine total biomass present in the slurry.
  e. Verify viability of both conidia and hyphae components using viable colony forming units of combined biomass slurry and a germination rate assay.

An assay of "viable colony forming units of combined biomass slurry" is a measure of discrete points of inoculation by incubating dilutions of the slurry liquid on a nutrient agar. The number of growing colonies after 24-72 hours indicates how many points of inoculation are present per unit of slurry volume.

A germination rate assay determines what percentage of conidia are viable and germinate (begin germ tube extension from conidia) after 24-48 hrs. This indicates the proportion of the inoculum that is viable as a result of conidia germination.

The assay can be conducted by different methods:

1. The first assay is a liquid culture incubated for 24 hrs and analyzed microscopically. The number of conidia forming germ tubes (germinating) are counted and the number of conidia not forming germ tubes (non-germinating) are counted until a total of at least 100 spores are counted. This is repeated 3 times for each replicate bottle and an average percentage of germinating conidia is calculated (germinating/total spores×100%).

2. The second method is similar to the "viable colony forming units" assay. The slurry liquid is filtered through a 40 micrometer screen to eliminate fragments of mycelium and results in a suspension of conidia. Serial dilutions out to 0.00001% of the original solution are then prepared and plated on nutrient agar. Plates are incubated for 24-72 hrs and the number of colonies is used to determine the number of viable conidia from the original sample conidia concentration.

Step 6—Qualification of Conidia/Hyphae Slurry for Use as an Inoculum

The conidia/hyphae slurry from the incubation vessel is combined with sterile water to dilute the biomass to an appropriate concentration for specific applications.
   a. Dilute to 0.1-5% for inoculation of a solid-state substrate.
   b. Dilute to 0.01-5% for inoculation of liquid substrate, for example, 1 part the biomass slurry and 99 parts water (a 100-fold dilution)

Figure 2:
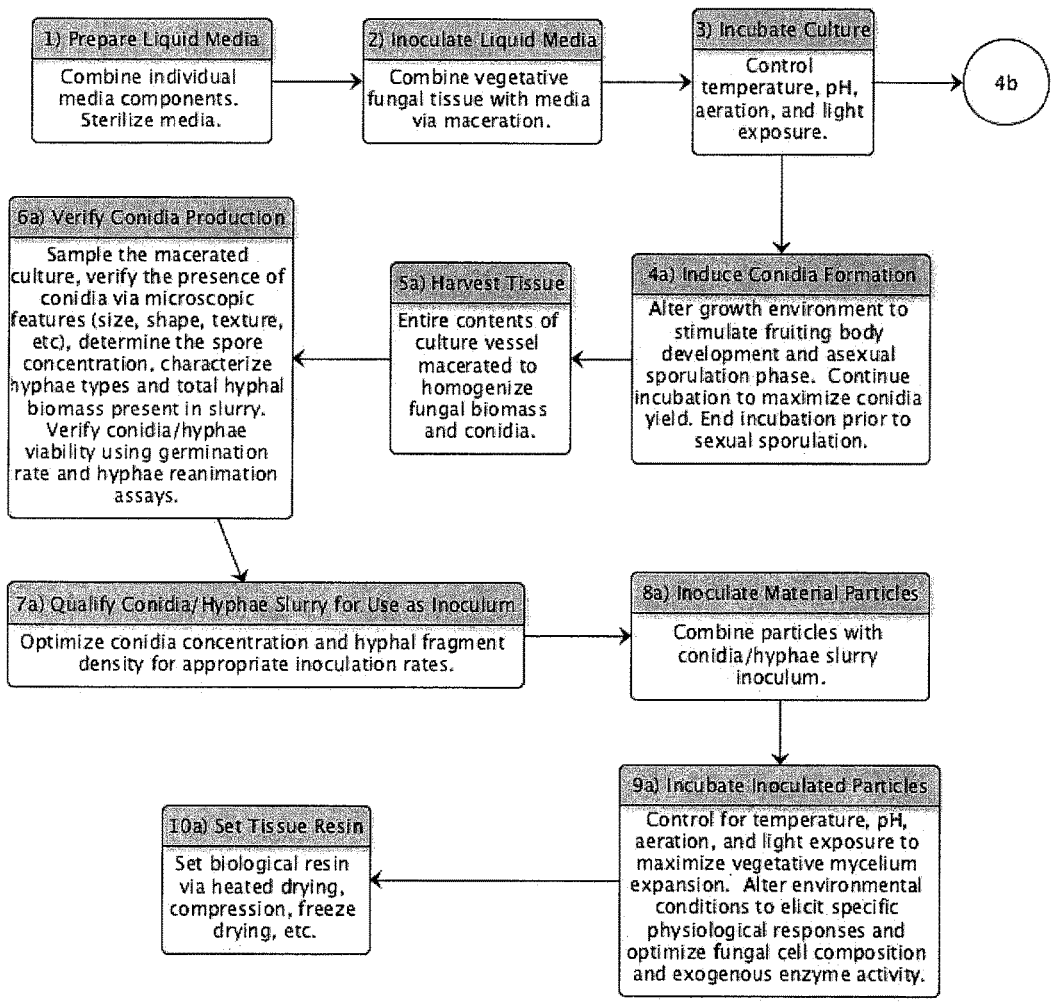
FIG. 2 illustrates a flow diagram of a process for making a binding resin biomass in accordance with the invention.

Referring to FIG. 2, the process for producing a biomass for use as a binding resin requires the following steps:

Step 1—Preparation of a Liquid Media.

A liquid growth medium is prepared as described above in step 1 of FIG. 1.

Step 2—Inoculation of Liquid Media

The sterile liquid growth medium is inoculated as described above in step 2 of FIG. 1.

Step 3—Incubation of Culture

The inoculated culture is incubated in a suitable vessel under strict environmental conditions, i.e.
   g. Growth temperature maintained between 20-30° C.
   h. pH of media buffered to maintain 5-7 during growth
   i. No exposure to light/UV
   j. Oxygen/carbon dioxide exchange within the culture vessel maintained to promote vegetative exponential growth
      a. 12-22% Oxygen
      b. 1-8% Carbon dioxide
   k. Time: until vegetative growth develops a homogeneous mycelium layer across the entire liquid surface, usually, between 5 and 7 days.

Step 4a—Induce Conidia Formation

The growth environment is altered to stimulate fruiting body (i.e. ascocarp) development and asexual sporulation phase, as above.
   Cycling of temperatures
   Cycling of oxygen/carbon dioxide concentrations
   Cycling of light/UV exposure Incubation is halted at maximum conidia production prior to the beginning of sexual sporulation as in step 3 of FIG. 1.

Step 5a—Harvesting of Biomass

The entire culture contents of the incubation vessel are macerated to homogenize fungal biomass and conidia as described above in step 4 of FIG. 1.

Step 6a—Verification of Conidia Production

The homogenized biomass is analyzed as described above in step 5 of FIG. 1.

Step 7a—Qualification of Conidia/Hyphae Slurry for Use as an Inoculum

The conidia/hyphae slurry from the incubation vessel is combined with sterile water as described above in step 6 of FIG. 1

Step 8a—Inoculation of Material Particles

The prepared conidia/hyphae slurry inoculum is aseptically combined with lignocellulosic particles in a mixing vessel to initiate fungal colonization.
   a. All lignocellulosic particle surfaces are covered with conidia/hyphae slurry liquid to assure homogenous colonization of substrate volume.
   The diluted inoculum is added at 10-30% of the overall water addition, which translates to 2-10% of the total batch mass (particles+liquid).
   Particle sizes can range from 0.125 inches to 0.75 inches.

Step 9a—Incubation of Inoculated Material Particles

The inoculated particles are incubated in a strictly controlled environment to optimize vegetative hyphae expansion, biomass accumulation, and enzymatic activity.
   a. Growth temperature maintained between 20-30° C.
   b. 12-22% Oxygen
   c. 1-8% Carbon dioxide
   d. Limited exposure to light/UV During this step, the temperature, pH, aeration and light exposure are controlled to maximize vegetative mycelium expansion for a time sufficient for hyphae to form a network around the particles and to form a cohesive biomass.

The environmental conditions are altered after the fungal biomass has homogeneously covered all particle surfaces to elicit specific physiological responses and to optimize fungal cell composition and exogenous enzyme activity.

The physiological responses can be inducement of pigmentation or mycelial surface morphologies for particular product aesthetics as well as changing the cellular chemical makeup to provide strength increases.

The exogenous enzyme activity alters the characteristics of the lignocellulosic particles to improve physical characteristics of the final product such as strength, water swell, screw hold, and the like.

This step is dependent upon the targeted final product. Time of completion of the step would be subject to appropriate quality control testing per application.

Step 10a—Setting of Tissue Resin

Figure 3:
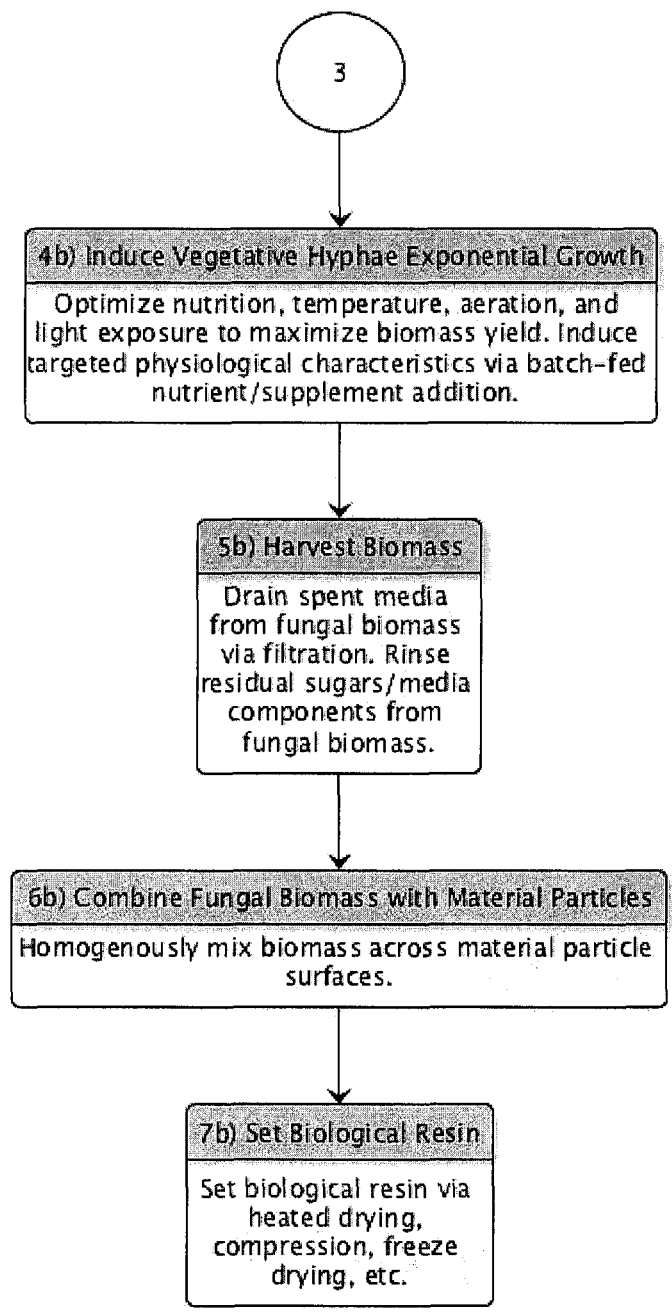
FIG. 3 illustrates a flow diagram of alternative steps in the process of FIG. 2 in accordance with the invention.

The accumulated biomass is set as a resin using methods specific to the desired product characteristics.
   a. Heated convection drying, heated compression, cold compression, freeze drying, microwave Referring to FIG. 3, the process of FIG. 2 may be modified so that the parameters of the growth chamber may be maintained to maximize hyphal exponential growth and generate fungal biomass.

Thus, after step 3 (incubation of culture) of the process of FIG. 2, the following steps are performed:

Step 4b—Induce Vegetative Hyphae Exponential Growth
   a. Introduce nutrients optimized for biomass production as a batch or fed-batch system.
   b. Maintain optimum growth temperatures
   c. Maintain dissolved oxygen levels with constant aeration of liquid media
   d. Strictly limit exposure of culture to light/UV
   e. Induce specific target characteristics of fungal biomass via staged nutrition addition and supplementation with induction additives During this step, the nutrition, temperature, aeration and light exposure are optimized to maximize biomass yield and to induce the specific target characteristics.

Step 5b—Harvest Biomass

The fungal biomass is separated from the spent culture media via filtration.
   a. Remove tissue biomass from spent media via filtration
   b. Wash residual sugars, media components, and metabolites from harvested biomass Step 6b—Combine Fungal Biomass with Material Particles The harvested biomass is mixed into the material particles to homogenously cover particle surfaces as in FIG. 2, step 8a. However, there is no need to sterilize the contents of the mixing vessel.

Step 7b—Set Biological Resin

The biomass/particle mixture is set as a resin using methods specific to the desired product characteristics.
   a. Heated convection drying, heated compression, cold compression, freeze drying, microwave

EXAMPLES

1. Production of Inoculum
   a. Bottles with 500 mL of malt extract broth were sterilized and aseptically inoculated by macerating half of a fully colonized malt extract agar plate culture, i.e. a *Xylaria polymorpha* into the media. The standard procedure is to use one full plate per liter of liquid.
   b. The bottles were shaken and placed at an angle to increase media surface area. With the cap loosened, the bottles were statically incubated at room temperature.
   c. After 5 to 7 days, a tissue sheet formed on the surface of the media and by day 15 the fruiting bodies had extended to about 2 centimeters (cm) in height. In this case, it is an important distinction that only half of the incubation time was required for the formation of a homogeneous vegetative mycelium sheet.
     The tissue sheet from one bottle was then aseptically transferred to a sterilized blender and macerated into 200 mL sterile water. This mixture was then poured back into the bottle.
   d. A sample of the mixture was aseptically removed and the spore concentration was determined to be $0.38 \times 10^6$ spores/mL using a Hemocytometer.
   e. This mixture was then used as the inoculum in Example 2.
   f. The other bottles were allowed to continue incubating to 48 days after inoculation with the tissue sheet on the surface producing fruiting bodies across more surface area.
   g. The entire culture vessel contents were then aseptically transferred to a sterilized blender and macerated to a homogenous mixture.
   h. A sample of the mixture was aseptically removed and the spore concentration was determined to be $3.59 \times 10^6$ spores/mL using a Hemocytometer.

FIGS. 4a and 4b illustrate photomicrographs of the tissue sheet of step c above after 15 days of incubation.

FIG. 4c illustrates a photomicrograph of isolated conidia from an ascocarp sampled prior to the maceration in step c above.

FIGS. 5a, 5b and 5c illustrate photomicrographs of the tissue sheet of step f above after 45 days of incubation and prior to maceration. These images show the continued development of the fruiting bodies and the increase in conidia formation.

2. Agricultural Waste Inoculated with Inoculum Produced in Example 1
   a. 500 g of corn stover as the agricultural waste and water were combined in a 5 L filter patch bag and sterilized at 15 psi and 121° C. for 1 hour. 1300 mL of water was added to hydrate the substrate to a suitable moisture content for facilitating mycelial growth.
   b. a 500 ml volume of the slurry prepared in Example 1 was then added to an agricultural waste substrate after cooling to room temperature to form a mixture.
   c. The bag was agitated to distribute the inoculum and tools, i.e. mold forms, were packed with 250 g of the substrate/slurry mixture.
   d. These tools were incubated at room temperature for 14 days before parts were removed and convection dried.
   e. Two one inch thick parts were stacked, heated and compressed to 0.25 inches to set the tissue resin.
   f. Mechanical strength as determined by the modulus of elasticity and modulus of rupture of the material. was then measured by using the standard 3-point bend test with an Instron Model 4411 and compared to an LD-1 Particleboard as defined by ANSI A208.1-1999 Particleboard (1999).

| Part | Density (lb/ft$^3$) | Elastic Modulus (psi) | Flexural Strength (psi) |
|---|---|---|---|
| *Xylaria* sp. | 38.66 | 157600 | 550 |
| LD-1 Particleboard | 35-40 | 79800 | 435 |

3. Biomass Production Comparison
   a. Bottles of malt extract broth (500 mL each) were prepared and sterilized at 15 psi and 121° C. for 1 hour.
   b. One bottle was inoculated with a polyporaceae species with aggressive vegetative growth and the other was inoculated with *Xylaria* sp.
   c. Inoculation was done aseptically by macerating half of a colonized agar plate culture into the media broth.
   d. Bottles were shaken and placed at an angle to increase broth surface area. With the bottle cap loosened, incubation was carried out statically at room temperature for 14 days.
   e. At the end of incubation, tissue sheets were removed from growth media and allowed to air dry to a constant mass.
   f. Dry mass yields were compared and *Xylaria* sp. produced 41% more dry mass than the polyporaceae species.

4 Tissue Added as Resin to Non-Colonized Particles
   g. Inoculate liquid media by macerating vegetative fungal tissue into the broth.
   h. Statically incubate culture at room temperature in a vessel with the maximum surface area per unit of broth volume.
   i. Once numerous ascocarps form on the tissue sheet surface (14-21 days), the tissue is removed from spent media and homogenized in liquid.
   j. The biomass slurry is then added to raw particles at a rate of 12% dry tissue mass to dry particle mass.
   k. Place mixture into mold of desired geometry.
   l. Set tissue resin through drying or compression.

5. Methods to Set Tissue Resin
   m. Static air drying (desiccation)
   n. Heated drying (convection, microwave)
   o. Freeze Drying
   p. Heated Compression
   q. Cold Compression 6. Casting Tissue Without Added Particles
   r. Inoculate liquid media by macerating vegetative fungal tissue into the broth.
   s. Statically incubate culture at room temperature in a vessel with the maximum surface area per unit of broth volume.
   t. Once numerous ascocarps form on the tissue sheet surface (14-21 days), the tissue is removed from spent media and homogenized in liquid.
   u. Place mixture into mold of desired geometry.
   v. Set tissue resin through drying or compression.

7. White Finish Engineered Wood
   w. Combine substrate particles to desired blend.
   x. Add supplemental nutrition: clear flour, calcium sulfate, spent brewers grain, algae waste, wheat bran, etc.
   y. Add water to reach a moisture content of 60-70%.
   z. Sterilize substrate blend at 15 psi and 121° C. for 1 hour.

aa. Dilute the inoculum prepared in Application A to 4.6×10$^5$ spores/mL and mix into sterile substrate.
bb. Incubate at room temperature, low O$_2$, and high CO$_2$ for 7-14 days.
cc. Dry material to 5-10% moisture and compress with added heat to a density of 40-60 lb/ft$^3$.
dd. Can apply light-colored facing material without background color affecting aesthetics.

8. Black Finish Engineered Wood
ee. Combine substrate particles to desired blend.
ff. Add supplemental nutrition: clear flour, calcium sulfate, spent brewers grain, algae waste, wheat bran, etc.
gg. Add water to reach a moisture content of 60-70%.
hh. Sterilize substrate blend at 15 psi and 121° C. for 1 hour.
ii. Dilute the inoculum prepared in Application A to 4.6×10$^5$ spores/mL and mix into sterile substrate.
jj. Incubate at room temperature with atmospheric O$_2$ and CO$_2$ for 7-14 days.
kk. Dry material to 5-10% moisture and compress with added heat to a density of 40-60 lb/ft$^3$.
ll. Black coloration can be aesthetically pleasing if no facing material is needed.

What is claimed is:

1. A process for generating a biomass comprising the steps of preparing a liquid media including a carbon source, a nitrogen source and micronutrients; inoculating the liquid media aseptically with a vegetative *Xylaria* fungal species to form a culture; statically incubating the culture in a vessel for a time sufficient to induce fruiting body development and asexual sporulation; halting said step of incubation at maximum conidia production prior to the beginning of sexual sporulation; and thereafter macerating the entire culture contents of the incubation vessel to homogenize the fungal biomass and conidia therein and form an inoculum.

2. A process as set forth in claim 1 wherein said step of statically incubating the culture includes maintaining the culture at a temperature between 20° C. and 30° C. and at a pH of from 5 to 7.

3. A process as set forth in claim 2 wherein said step of statically incubating the culture includes maintaining an oxygen/carbon dioxide exchange within the vessel to maintain an oxygen level from 12 to 22% oxygen and a carbon dioxide level of 1 to 8% carbon dioxide.

4. A process as set forth in claim 1 wherein said step of inoculating the liquid media is at an amount of 0.01% to 5% m/v of vegetative *Xylaria* fungal species to liquid media.

5. A process as set forth in claim 1 wherein said vegetative *Xylaria* fungal species is selected from the group consisting of *Xylaria polymorpha*, *Xylaria hypoxylon*, *Xylaria filiformis* and *Xylaria longipes*.

6. A process as set forth in claim 1 wherein said step of statically incubating the culture is conducted until vegetative growth develops a homogeneous mycelium layer across an entire surface of said liquid media and continued with an altered incubation environment to induce fruit body development and asexual sporulation.

7. A process as set forth in claim 6 wherein said step of statically incubating the culture is conducted for a time period between 5 and 7 days until vegetative growth develops said homogeneous mycelium layer.

8. A process as set forth in claim 6 wherein said altered incubation environment includes cycling of temperatures from 15° C. to 30° C. in 12 hour periods to mimic day/night cycles, cycling of oxygen/carbon dioxide concentrations to maintain atmospheric oxygen and carbon dioxide levels and cycling of light/UV exposure from no light exposure to 6 to 18 hours of light exposure followed by a period of no light exposure.

9. A process as set forth in claim 1 further comprising the steps of combining the inoculum with lignocellulosic particles to initiate fungal colonization of the particles; incubating the inoculated material particles for a time sufficient for hyphae to form a network around the particles and to form a cohesive biomass; thereafter setting the biomass as a resin.

10. A process as set forth in claim 9 wherein said particles are of a size of from 0.3 cm to 2 cm.

11. A process as set forth in claim 9 wherein said step of incubating includes maintaining the growth temperature between 20° C. and 30° C., an oxygen level of from 12% to 22%, a carbon dioxide level of from 1% to 8% and a limited exposure to light/UV.

12. A process as set forth in claim 1 further comprising the steps of combining the inoculum with lignocellulosic particles to initiate fungal colonization of the particles; incubating the inoculated material particles for a time sufficient for hyphae to form a network around the particles and to form a cohesive biomass; removing the biomass from spent media; washing residual media components from the biomass; combining the biomass with material particles to initiate fungal colonization of the particles; incubating the combined biomass and material particles for a time sufficient for hyphae to form a network around the particles and to form a cohesive biomass; and thereafter setting the cohesive biomass as a resin.

13. A process for generating a biomass comprising the steps of preparing a liquid media including a carbon source, a nitrogen source, micronutrients and a vegetative *Xylaria* fungal species to form a culture; statically incubating the culture in a vessel maintained in an incubation environment until vegetative growth develops a homogeneous mycelium layer across an entire surface of said liquid media in the vessel; thereafter altering said incubation environment to induce fruit body development and asexual sporulation; thereafter halting said step of incubation at maximum conidia production prior to the beginning of sexual sporulation; and thereafter macerating the entire culture contents of the incubation vessel to homogenize the fungal biomass and conidia therein and form an inoculum.

14. A process as set forth in claim 13 wherein said step of statically incubating the culture is conducted for a time period between 5 and 7 days until vegetative growth develops said homogeneous mycelium layer.

15. A process as set forth in claim 13 wherein said step of incubating includes maintaining the growth temperature between 20° C. and 30° C., an oxygen level of from 12% to 22%, a carbon dioxide level of from 1% to 8% and a limited exposure to light/UV.

16. A process as set forth in claim 15 wherein said step of altering said incubation environment includes cycling of temperatures from 15° C. to 30° C. in 12 hour periods to mimic day/night cycles, cycling of oxygen/carbon dioxide concentrations to maintain atmospheric oxygen and carbon dioxide levels and cycling of light/UV exposure from no light exposure to 6 to 18 hours of light exposure followed by a period of no light exposure.

17. A process as set forth in claim 13 wherein halting said step of incubation occurs in response to ascocarps dropping a visible layer of conidia from the fruiting bodies.

18. A process as set forth in claim 17 wherein dropping a visible layer of conidia from the fruiting bodies occurs between 14 and 21 days of said step of incubation.

\* \* \* \* \*